United States Patent
Davis et al.

(10) Patent No.: US 10,564,153 B2
(45) Date of Patent: Feb. 18, 2020

(54) DEVICE FOR DETECTING MISFOLDED PROTEINS AND METHODS OF USE THEREOF

(71) Applicant: GestVision, Inc., Guilford, CT (US)

(72) Inventors: Wendy L. Davis, Guilford, CT (US); Daniel Levenson, La Mesa, CA (US)

(73) Assignee: Gestvision, Inc., Guilford, CT (US)

( * ) Notice: Subject to any disclaimer, the term of this patent is extended or adjusted under 35 U.S.C. 154(b) by 32 days.

(21) Appl. No.: 15/211,957

(22) Filed: Jul. 15, 2016

(65) Prior Publication Data

US 2017/0016891 A1 Jan. 19, 2017

Related U.S. Application Data

(60) Provisional application No. 62/192,962, filed on Jul. 15, 2015.

(51) Int. Cl.
*G01N 33/543* (2006.01)
*G01N 33/68* (2006.01)

(52) U.S. Cl.
CPC ..... *G01N 33/54366* (2013.01); *G01N 33/689* (2013.01); *G01N 33/6896* (2013.01); *G01N 2800/2828* (2013.01); *G01N 2800/2835* (2013.01)

(58) Field of Classification Search
CPC ......... G01N 33/54366; G01N 33/6893; G01N 33/6869; G01N 33/689; G01N 2800/2835; G01N 2800/2828
See application file for complete search history.

(56) References Cited

U.S. PATENT DOCUMENTS

| | | | | |
|---|---|---|---|---|
| 5,252,496 A | * | 10/1993 | Kang | ............... G01N 33/54366 435/5 |
| 5,451,504 A | * | 9/1995 | Fitzpatrick | ........... G01N 33/558 435/7.2 |
| 5,804,452 A | * | 9/1998 | Pronovost | ................ C12Q 1/26 422/420 |
| 6,485,982 B1 | | 11/2002 | Charlton | |
| 2010/0330585 A1 | | 12/2010 | Kabir et al. | |
| 2011/0280863 A1 | * | 11/2011 | Buhimschi | ........... G01N 33/689 424/130.1 |
| 2014/0044796 A1 | | 2/2014 | Kehrel et al. | |

FOREIGN PATENT DOCUMENTS

WO 2014/124392 A1 8/2014

OTHER PUBLICATIONS

International Search Report for corresponding PCT application No. PCT/US16/42426 dated Oct. 5, 2016.
(Continued)

*Primary Examiner* — Krishnan S Menon
*Assistant Examiner* — Dwan A Gerido
(74) *Attorney, Agent, or Firm* — Wood, Phillips, Katz, Clark & Mortimer

(57) ABSTRACT

The present invention relates to diagnostic devices as well as methods of using these devices for detecting proteins of interest associated with diseases or disorders in mammals. In particular, the proteins of interest may be misfolded proteins associated with certain misfolded-protein disorders in mammals including those mammals suspected of or at risk of having such disorders.

16 Claims, 5 Drawing Sheets

Looking down on device strip

(56) References Cited

OTHER PUBLICATIONS

Buhimschi Irina et al: "20: Assessment of global protein misfolding load by urine "Congo Red Dot" test for diagnosis and prediction of outcome in women with preeclampsia (PE)", American Journal of Obstetrics & Gynecology, vol. 201, No. 6, Dec. 1, 2009.
Jing Hongwu et al: "781: Protein enrichment using Congo red (CR) affinity enhances characterization of the urine misfoldome in preeclampsia (PE)", American Journal of Obstetrics & Gynecology, vol. 214, No. 1, S408, Jan. 1, 2016.
Rood Kara et al: 34: Point-of-care conga red dot (CRD) test for antenatal triage and rapid identification of preeclampsia ( PE) II. American Journal of Obstetrics & Gynecology, vol. 214, No. 1, S24-S25, Jan. 1, 2016.
Buhimschi et al: Protein misfolding, congophilia, oligomerization, and defective amyloid processing in preeclampsia11 , Science Translational Medicine, vol. 6, No. 245, Jul. 16, 2014.
Buhimschi I A et al: 239: Preeclampsia is a disease characterized by specific supramolecular aggregates of misfolded proteins and congophilia11 , American Journal of Obstetrics & Gynecology, Mosby, St Louis, MO, US, vol. 199, No. 6, p. 1-15, Dec. 1, 2008.
Extended European Search Report dated Dec. 7, 2018 issued by EPO in EPA No. 16825235.1.

\* cited by examiner

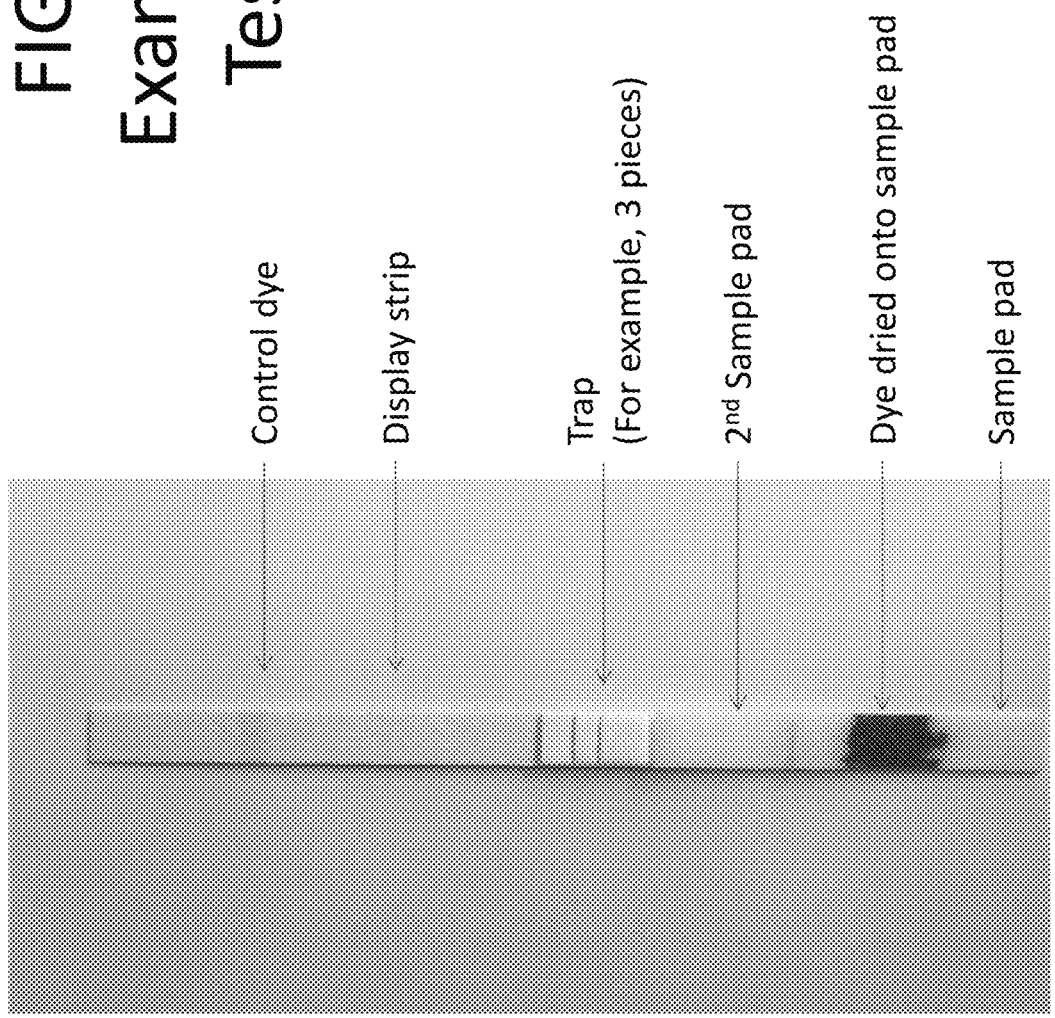

FIGURE 3: Components of Test Strip

Sample pad Trap    Display strip

Looking down on device strip

Device strip from the side
Materials may be butted together

Alternative configuration:
Materials may overlap (view of side edge)

FIGURE 4: Trap Configurations Within Test Strip

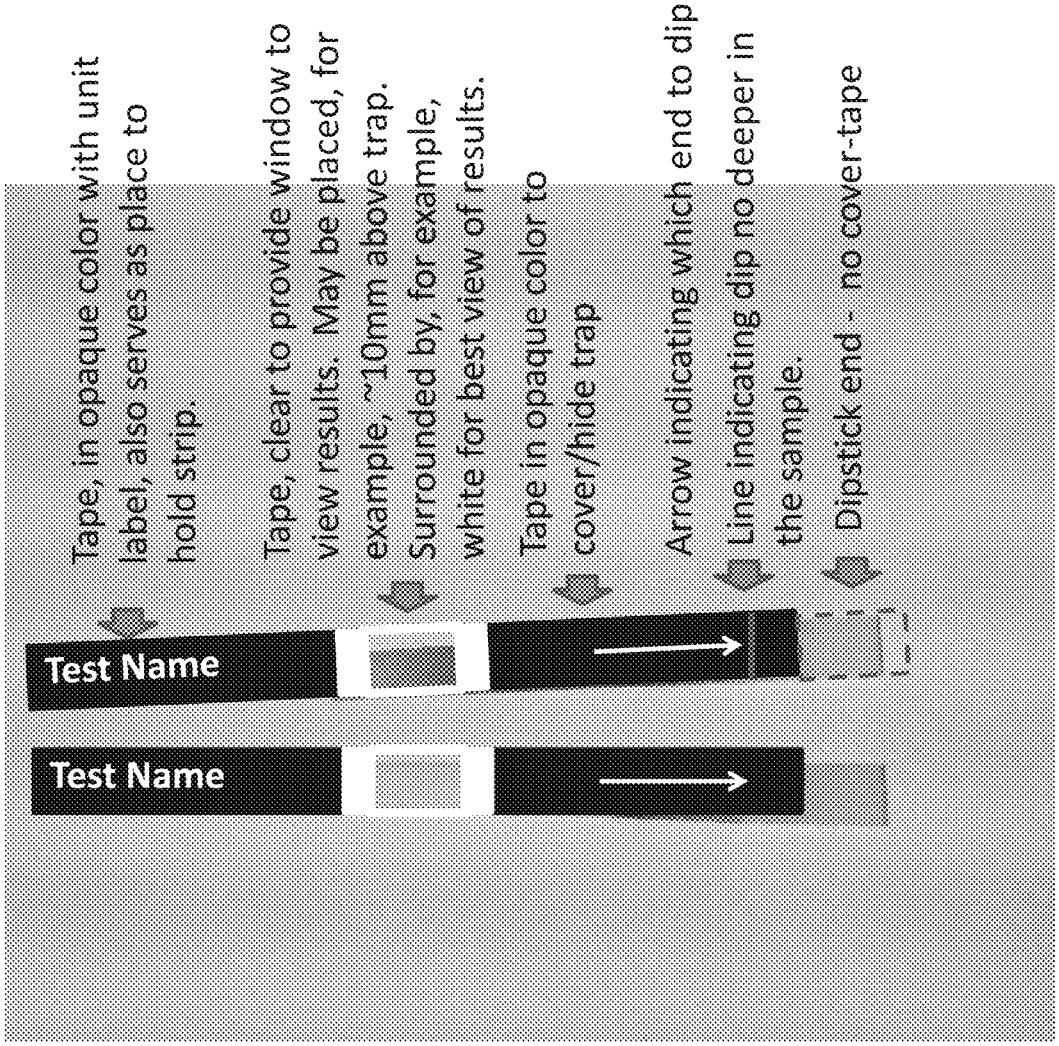
FIGURE 5: Example of Dipstick Configuration

DEVICE FOR DETECTING MISFOLDED PROTEINS AND METHODS OF USE THEREOF

BACKGROUND OF THE INVENTION

According to the American College of Obstetricians and Gynecologists, hypertensive disorders of pregnancy including preeclampsia complicate approximately 10% of pregnancies throughout the world and are a leading cause of maternal and fetal morbidity and mortality [ref: Hypertension in Pregnancy, Report of the American College of Obstetricians and Gynecologists' Task Force on Hypertension in Pregnancy, Obstetrics and Gynecology 122 Vol. 122, No. 5, November 2013 (the ACOG 2013 guildelines)]. Furthermore, these conditions are a leading cause of premature births and associated perinatal complications [ref: Ananth C V, Vintzileos A M. J Matern Fetal Neonatal Med. 2006:19(12):773-82]. Hypertension in pregnancy can be categorized as 1) preeclampsia-eclampsia, 2) chronic hypertension 3) chronic hypertension with superimposed preeclampsia or 4) gestational hypertension.

Preeclampsia-eclampsia is a poorly understood pregnancy-related condition that is a leading cause of maternal mortality, premature birth, and rising healthcare costs for maternity. Globally, the death of 76,000 expectant mothers is due to preeclampsia. Preeclampsia is responsible for one-fifth of deaths related to pregnancy in the U.S., and the condition can lead to seizures, organ failure and death. It most commonly occurs after about 20 weeks of pregnancy, and women are at risk through the postpartum period. The condition can result in seizures or convulsions known as eclampsia. Preeclampsia may be categorized as mild, severe, less severe, more severe or as preeclampsia without severe features, or preeclampsia with severe features. HELLP syndrome, a preeclampsia subtype, is characterized as patients with symptoms of hemolysis, elevated liver enzymes and low platelet count. Preeclampsia that presents with an unusual compilation of symptoms is known as atypical preeclampsia.

The only known cure is to deliver the baby, and as a result, preeclampsia is the leading cause of pre-term births that are medically indicated, estimated to be 17% of all preterm births. Costs to the U.S. healthcare system are estimated to be over $13 billion for delivery and care of mother and infant due to preeclampsia. Today, preeclampsia remains a challenge to diagnose, as it is characterized only by its symptoms: most often, high blood pressure and the presence of urine protein. Research towards improving the diagnosis of preeclampsia has commonly searched for known biomarkers in blood which are up- or down-regulated, but few if any findings have yielded globally useful diagnostic products.

Research utilizing urine specimens of women with severe preeclampsia that required medically indicated delivery due to a diagnosis of preeclampsia (MIDPE) and an unbiased mass spectrometry protein profiling approach and found unique non-random cleavage products of SERPINA-1 and albumin. Knowledge of the tendency of SERPINA-1 fragments to misfold and form supramolecular aggregates led to the proposal that preeclampsia may be a misfolding disorder, not unlike Alzheimer's disease [See U.S. Pat. No. 8,263,342 and Buhimschi et al., *Am J Obstet Gynecol.* 2008 November; 199(5): 551.e1-551.16. doi:10.1016/j.ajog.2008.07.006.]

Furthermore, misfolded protein based on binding of the proteins to Congo Red (CR) dye ("congophilia") were found in urine from women with preeclampsia. These misfolded protein(s) or "supramolecular aggregates" bound to conformational state-dependent anti-amyloid aggregate antibodies were associated with a highly active amyloid precursor protein (APP) processing pathway and amyloid-like protein deposits in placentas from preeclamptic women. [See Buhimschi et al., *Sci. Transl. Med.* 6, 245ra92 (2014).] A dot blot affinity assay measured the proportion of CR retained (due to binding to misfolded protein) after washing (as % of original CR) and results were reported as % Congo Red Retention (CRR).

In a feasibility study of 80 women (40 who required medically indicated delivery and 40 were "control" healthy pregnancies), % CRR was significantly higher in severe preeclampsia urine (P<0.001) with 100% sensitivity and specificity. In a validation study of 582 women (in cross sectional and longitudinal cohorts), women with severe preeclampsia and preeclampsia superimposed on existing high blood pressure or proteinuria had higher % CRR than all other clinical classifications (P<0.001). Furthermore, 75% of women diagnosed with mild preeclampsia, 89% with severe preeclampsia and 91% with superimposed preeclampsia had CRR results higher than all other groups (P<0.05). Overall, CRR alone in the validation cohort had 85.9% sensitivity and 85.00 specificity, positive likelihood ratio of 95% and negative likelihood ratio of 95% in prediction of preeclampsia necessitating MIDPE. CRR was superior to clinical screening methods currently used for preeclampsia (P<0.001 compared to blood pressure or urine protein dipstick; P=0.004 compared to combined blood pressure combined with urine protein at American College of Obstetricians and Gynecologists (ACOG) recommended cutoffs) (Buhimschi et al., *Sci. Transl. Med.* 6, 245ra92 (2014) and U.S. Pat. No. 9,229,009.)

Congo Red also binds to cellulose which was used to create a simple paper based assay. Normal urine-dye mixtures applied to test paper results in dye binding to the cellulose in the paper visualized as a red tightly centered dot. In contrast, urine from women with congophilic urine proteins results in the dye no longer binding to cellulose because it is bound to the proteins and instead dispersing in a diffuse fashion visualized as a halo. (See U.S. Patent Application Publication No. 20150293115.) In a clinical study of 346 women referred to a labor and delivery triage center to rule-out preeclampsia, patient urine was tested using the CR simple paper assay (CRD). The CRD test demonstrated a 79% sensitivity 89% specificity, negative predictive value of 91%, positive predictive value of 74% for the diagnosis of preeclampsia as defined by the ACOG 2013 guidelines [ref: Rood et al 2016 AJOG Volume 214, Issue 1, Supplement, Pages S24-S25]. The CRD test requires a step of mixing urine with dye before applying the urine to the test paper and the results can be challenging to read and interpret.

In view of the above, there is still a highly significant and unmet need for a simple diagnostic device that may be used at the point of care to detect possible preeclampsia in pregnant mammals and especially women. Such a device could potentially save the lives of thousands of pregnant women as well as their unborn fetuses by providing early information as to whether a woman is at risk for preeclampsia or has preeclampsia and should therefore receive immediate therapeutic intervention.

All patents and publications referred to herein are hereby incorporated in their entirety by reference.

BRIEF SUMMARY OF THE INVENTION

The present invention includes a diagnostic device for detection of at least one protein in a biological sample of a mammal. The device comprises a) a sample receiving material, wherein the sample receiving material is capable of receiving a biological sample; b) a detection reagent, which is reactive with (i.e., binds to) at least one protein present in the biological sample; c) a trap which is in contact with the sample receiving material and is able to separate the detection reagent bound to the at least one protein in the biological sample from the detection reagent that is not bound to the at least one protein in the biological sample, whereby the detection reagent bound to the at least one protein in the biological sample is able to flow through the trap, and whereby the detection reagent that is not bound to the at least one protein in the biological sample is captured by the trap; d) a capillary bed which is in contact with the trap, and is configured to contain the biological sample after the biological sample flows through the trap. The capillary bed displays the bound detection reagent if the at least one protein is detected in the biological sample. The sample receiving material, trap, and capillary bed are configured to be in contact in sequence. The sample receiving material of the device may comprise, for example, the detection reagent. Also, the detection reagent may be on or within the sample receiving material.

Further, the device may be encased in a housing or cassette. The housing or cassette may comprise a well (or other entity) for biological sample application and may also contain a window for reading the results obtained. The device may be used at the point of care in a variety of clinical and non-clinical settings or in a clinical laboratory.

As noted above, the detection reagent binds to at least one protein in the biological sample. This at least one protein may be, for example, a misfolded protein, a protein aggregate, a supramolecular protein aggregate as well as mixtures thereof and fragments of each protein. The at least one protein may comprise a beta sheet structure. Additionally, the at least one protein may be congophilic. The misfolded protein may comprise, for example, alpha-1 antitrypsin (SerpinA1), ceruloplasmin, heavy-chain IgG, light-chain IgG, interferon-inducible protein 6-16 (IF16-6, G1P3), albumin, mixtures thereof or fragments thereof, or fragments of each protein. However, the misfolded protein is not limited to these proteins. For example, the misfolded protein may be any protein (or combination of proteins) which causes or is associated with a protein-misfolding disorder.

The detection reagent may be, for example, an azo dye, Thioflavin T or an analog of an azo dye. An example of an azo dye that may be utilized in connection with the present invention is Congo Red (i.e., disodium 4-amino-3-[4-[4(1-amino-4-sulfonato-naphthalen-2-yl)diazenylphenyl]phenyl] diazenyl-naphthalene-1-sulfonate). (An analog of Congo Red may also be utilized. For example, secondary diazo dyes of the formula $C_{32}H_{22}N_6Na_2O_6S_2$ may also be used as the detection reagent described herein in connection with the device of the present invention.) The Congo Red may be pre-loaded onto the sample receiving material referred to above.

The sample receiving material of the device of the present invention may comprise, for example, nitrocellulose, cellulose, a glass fiber, cotton, a woven mesh, a nonwoven material, a porous plastic, a polymer and/or a polyester. The polyester may be, for example, polyethylene.

The trap of the device of the present invention may comprise, for example, nitrocellulose, cellulose, a glass fiber, a cotton/glass fiber, a woven mesh, a nonwoven material, a polymer, and/or a polysulfone.

The capillary bed of the device of the present invention may comprise a material such as, for example, nitrocellulose, a chromatographic paper, polysulfone and/or cellulose.

It should be noted that the device of the present invention provides a test result in approximately 10 minutes or less, preferably approximately 5 minutes or less, more preferably approximately 3 minutes or less, and most preferably 1 minute or less. Further, one may obtain a qualitative or semi-quantitative result by visualization. Moreover, one may also obtain a semi-quantitative or quantitative result such that the amount of the at least one protein is measured, if desired.

The present invention also includes a diagnostic device, as described above, which is utilized for the detection of misfolded protein in a biological sample, for the detection of aggregated protein in a biological sample and/or for the detection of supramolecular aggregated protein in a biological sample, wherein the sample is obtained from a mammal, for example, a human, primate or genetically-engineered mammal. In some instances, the mammal may be pregnant. The device, as described above, may be used for the detection of preeclampsia which may be diagnosed when the detection reagent is reactive (i.e., binds) to a misfolded protein, aggregate protein and/or supramolecular aggregate protein (i.e., proteins associated with preeclampsia in pregnant mammals) contained with the biological sample. The trap of the device may be configured to competitively bind to the detection reagent of the device. The device may be configured as a lateral flow device or a strip comprising the sample receiving material, the trap and the capillary bed.

Additionally the present invention encompasses a method of detecting at least one protein in a biological sample of a mammal comprising the steps of: a) applying a biological sample of said mammal to the sample receiving material of the diagnostic device of the present invention for a time and under conditions sufficient to allow the at least one protein to bind to the detection reagent; and b) detecting presence of detection reagent on the capillary bed, wherein presence of detection reagent on the capillary bed indicates presence of the at least one protein present in said biological sample.

The method may be utilized for detecting at least one protein in a biological sample of a mammal having a protein-misfolding disorder or at risk of having a protein-misfolding disorder. This method comprises the steps of: (a) applying a biological sample of the mammal to the sample receiving material of the diagnostic device described above for a time and under conditions sufficient to allow the at least one protein to bind to the detection reagent and (b) detecting presence of bound detection reagent on the capillary bed, wherein presence of detection reagent on the capillary bed indicates presence of the at least one protein present in the biological sample, and indicates that the mammal has the protein-misfolding disorder. Again, the at least one protein may be, for example, a misfolded protein, an aggregated protein, a supramolecular aggregated protein, or a mixture thereof, or a protein with a beta sheet structure, such as a congophilic protein. The at least one protein may be congophilic and/or may have a beta sheet structure. More specifically, the misfolded protein may be, for example, alpha-1 antitrypsin (SerpinA1), ceruloplasmin, heavy-chain IgG, light-chain IgG, interferon-inducible protein 6-16 (IF16-6, G1P3), albumin, mixtures or fragments thereof, or fragments of each protein. The protein-misfolding disorder may be, for example, preeclampsia, Alzheimer's disease, prion disease or Parkinson's disease. Misfolded proteins found in other diseases or conditions characterized as protein-misfolding disorders may also be detected using the device of the present invention. As to the diagnosis of preeclampsia using the device of the present invention, one may diagnose different forms of preeclampsia including, for example, mild preeclampsia, severe preeclampsia, atypical preeclampsia, hemodialysis-elevated liver enzyme-low platelet count (HELLP) syndrome and eclampsia. Further, a patient may be suffering from a hypertensive disorder of pregnancy. Thus, the present method may be utilized to differentially diagnose certain hypertensive disorders of pregnancy such as differentiating preeclampsia from hypertensive conditions such as chronic hypertension or gestational hypertension or hypertension due to other causes, or differentiating the types of preeclampsia noted above.

The biological sample used in the above method and applied to the sample receiving pad may be, for example, urine (clean or natural catch), blood, saliva, tissue, interstitial fluid, serum, plasma, cerebrospinal fluid, amniotic fluid or an extracted substance (e.g., extracted from nasal secretions, ear wax, fecal material and tissue). The method is utilized in connection with biological samples from mammals, for example, humans, primates and genetically-engineered mammals. The mammal may be pregnant. In the case of a human, the method may be utilized in connection with a pregnant woman who is approximately 8 to 42 weeks pregnant (i.e., gestational age), preferably about 18 to 41 weeks pregnant, and more preferably about 20 to 41 weeks pregnant or 20 weeks to delivery. However, the method of the present invention may also be utilized in connection with a postpartum mammal. It should be noted that the least one protein detected by the method, utilizing the device, may be detected by visualization in order to obtain a qualitative or semi-quantitative result or detected by measurement in order to obtain a semi-quantitative or a quantitative result. Subsequent to visualization, the at least one protein may be measured in order to obtain a semi-quantitative or a quantitative result.

Additionally, the present invention includes a kit comprising the above-described device. This kit may also comprise a calibrator or control reagent as well as instructions for use of the device. Also, the kit may comprise a sample applicator.

BRIEF DESCRIPTION OF THE DRAWINGS

FIG. 2 shows an example of a test strip embodiment of the inventive device. The strip comprises a control dye, a display strip (or capillary bed), a trap (e.g., three pieces of material), a second sample pad (or sample receiving material), a first sample pad (or sample receiving material) and the dye dried onto the sample pad.

FIG. 3 shows an embodiment of the diagnostic device of the present invention.

FIG. 4 shows different material configurations within the test strip.

FIG. 5 shows an example of a dipstick configuration of the test strip of the present invention. This embodiment is configured with a cover tape on top of the test strip. At the top of the test strip, the tape is opaque in color and may be used to hold the strip. In the middle, the tape is clear to provide a viewing window for the results. The tape may be placed so that the clear window is, for example, approximately 10 mm above the trap. The tape at the window may be surrounded by a color (e.g., white) which allows for easy viewing of the results. Below the trap, the tape is opaque in color to cover the trap. At the bottom of the strip, the tape may display an arrow indicating which end of the strip to dip into the test sample and may display a line indicating the maximum level to dip the test strip into the sample. The bottom end of the test strip may be free of cover tape to facilitate wicking of test sample upon dipping.

DETAILED DESCRIPTION OF THE INVENTION

Figure 1:
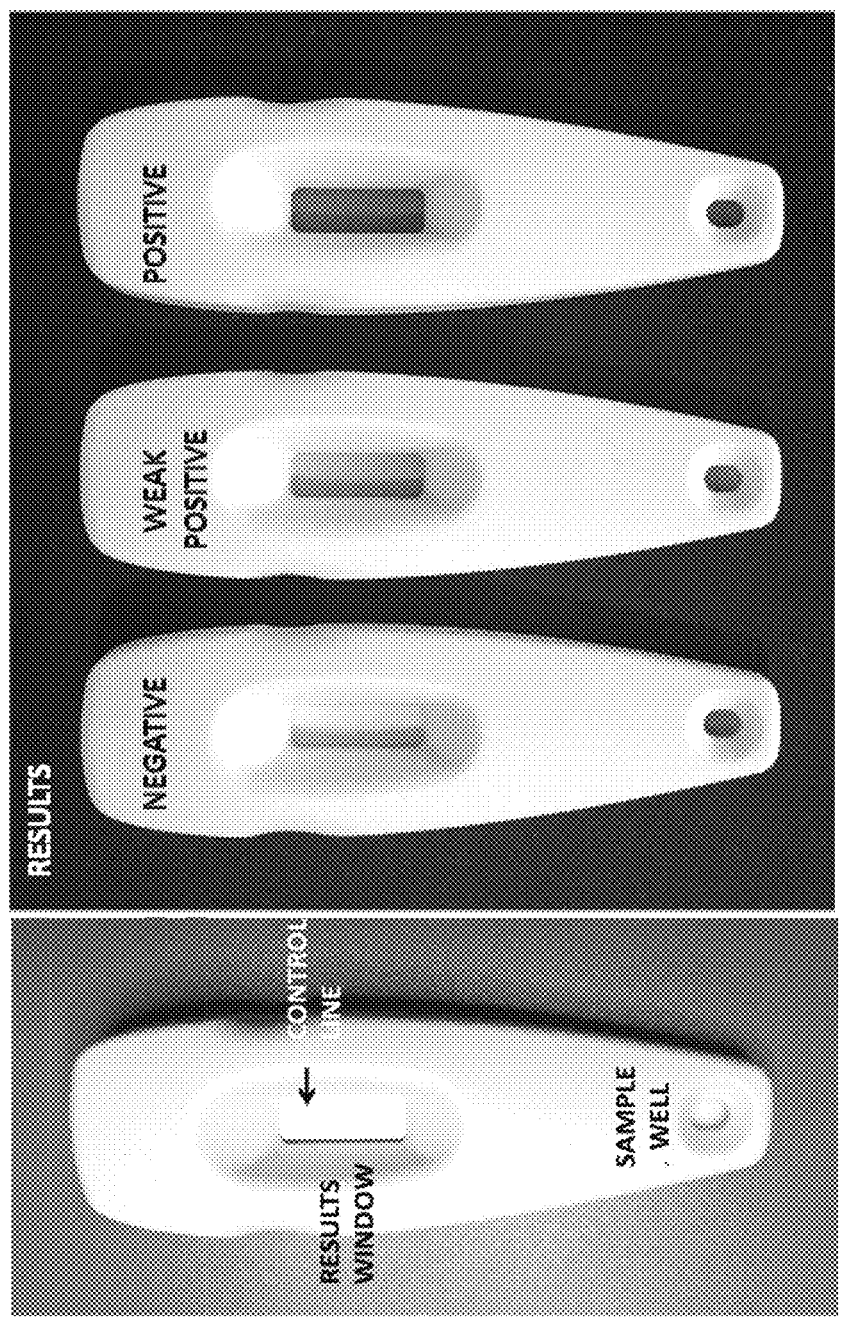
FIG. 1 shows photographs of device test strips of the invention in a cassette or housing. The left panel of FIG. 1 illustrates the device in a housing prior to contact with a biological sample, with a sample well, a results window and control line. The right panel shows the device results of testing urine samples known to be negative, weak positive and positive for misfolded proteins associated with preeclampsia.

The present invention is a device as well as methods of utilizing this device. More specifically, the device is a lateral flow chromatographic rapid test that may be used in several clinical and non-clinical settings in order to detect proteins of interest in a biological specimen. The device may be used to detect protein-misfolding disorders in mammals. The mammal may be suspected of having or at risk of having one or more such disorders.

The device has several, different embodiments which will be described herein. Basically, it comprises a test strip for detection of a protein or proteins of interest in a biological sample (see, for example, FIG. 1). The detection is carried out by means of a sequential series of reactions. The test strip comprises a length of lateral flow assay or chromatographic material having capillarity and has a first end at which chromatographic solvent transport begins. It also has a second end at which chromatographic solvent transport ends. The strip includes a plurality of zone or regions which are positioned between the first and second ends (see, for example, FIGS. 2 and 3). The zones include a first zone which is impregnated with a detection reagent, for example, a dye. This detection reagent specifically binds with the protein or proteins of interest in the biological sample. The first zone also receives the biological sample. In comparison, the second zone, which is downstream of the first zone, retains the detection reagent which is not bound to the protein or proteins of interest in the biological sample while permitting detection reagent bound to the protein or proteins of interest in the biological sample to be transported to a third zone. The third zone of the test strip, located downstream of the second zone, receives the sample after it passes through the second zone. The third zone will display the detection reagent if the proteins of interest are present in the sample. It also comprises a means for detecting the detection reagent bound protein as a measure of the protein or proteins in the biological sample. In one embodiment, the device determines the presence of misfolded proteins in the biological sample from a patient and allows for determination of whether a patient has or does not have a protein-misfolding disorder. The presence of the protein or proteins can be qualitatively or semi-quantitatively determined via visualization or may be semi-quantified or quantified by use of a measuring entity which may be present within the device. After the biological sample is applied to the first zone, the first zone releases the detection reagent in the sample, and the second zone separates the detection reagent bound to the protein or proteins from unbound detection reagent, and permits only bound detection reagent to be transported to the third zone which then displays the bound detection reagent for viewing or measurement. The first zone may be a sample receiving material. The second zone may be a trap. The third zone may be a capillary bed or display strip.

The specific elements or components of the device and the characteristic or properties of these elements are described, in detail, as follows:

Materials Used in Components of Device

The sample receiving material, the trap, and the capillary bed can be made from the same or different materials. The materials are generally known in the art of lateral flow devices and chromatography [see Ref: EMD Millipore Rapid Lateral Flow Test Strips Considerations for Product Development, available from EMD Millipore, Billerica, Mass.]. Membranes are selected based on physical and chemical properties that impact capillary flow and therefore reagent deposition and assay performance. The materials include, for example, but are not limited to, nitrocellulose, filter papers, chromatography papers, cellulose, plastic polymers, asymmetric polysulfone membrane, cotton, linters and/or glass fibers, polyesters, polyethylene and polysulfone. Membranes may be made of polymers including, for example, nitrocellulose, polyvinylidene fluoride, nylon and polyethersulfone. Pad materials are often used as sample receiving material to provide controlled and even receipt of the sample and facilitate flow to the contiguous strip materials of the device. The pad materials are porous, often made with cellulose (i.e. filter papers), glass fibers, woven meshes and synthetic nonwoven material or polyesters. Filter matrices may be used for sample receipt particularly if it is desirable to separate out extraneous material contained in the sample from that part of the sample to be assayed, for example, to separate out cellular material from fluid. These filter matrixes may be, for example, cellulose, asymmetric polysulfone membrane (including but not limited to Vivid™ Plasma separation membrane and asymmetric sub-micron (BTS) polysulfone membrane). Absorbent pads may be used, for example, as a wick at the end of the device strip to pull sample through the lateral flow strip, and may increase the amount of sample assayed and enhance assay sensitivity. These absorbent pads are often cellulose or cotton linters and optimally selected based on thickness, compressibility, and uniformity of bed volume. The entire strip may be assembled on a backing card often a card of a plastic backing and adhesive. While these various materials are often thought of for specific purposes in lateral flow devices, as described herein, each material may be considered for suitable properties for the purposes of the receiving material, trap and display strip of the present invention. See Examples for further discussion of materials.

Other materials utilized in the configuration of the test strip, specifically the display strip, are known in the art of lateral flow technology and chromatography.

Elements or Components of the Device

Sample Receiving Material (Sample Pad)

The first element of the device (hereinafter referred to as the sample receiving material or the sample pad) acts as a sponge and holds an excess of sample fluid to be tested. The receiving material absorbs sample, but also permits it to flow or to wick to the next contiguous material. It is typically inert to, and thus does not react with, proteins of interest that may be present in the sample, as well as the detection reagent (e.g., dye), allowing proteins and detection reagent to flow or to wick through the material to contiguous material in the lateral flow device.

The sample receiving material may be dipped into the sample from the mammal or patient or, alternatively, the sample may be indirectly or directly applied to the sample receiving material. The sample may be applied to the sample receiving material by, for example, a dropper with a metered tip, a pipette, a transfer pipette, or a pipette capable of repeated dispensing of the patient sample. If the sample receiving material is configured to be dipped into the biological sample, (see FIG. 5, for example), then the sample receiving material may be relatively long (for example, but not limited to, about 10 mm). If the sample receiving material is configured to receive the sample, applied by, for example, a dropper or pipette, then the sample receiving material may be relatively short (between, but not limited to, about 5 mm and about 10 mm). Commonly, the width may be from 2 mm to 10 mm, and most commonly, 2.5 to 5 mm (+0.5 mm). Variations in the length and width of the sample receiving material are possible and depend upon such factors as the size of the cassette or housing as well as the ability of the biological sample to sufficiently mix with the detection reagent.

In particular, the sample receiving pad acts as a capillary matrix in which the biological sample and a detection reagent (e.g., dye) can freely mix. The sample pad may also have a detection reagent in a dried format suitable for an optimized chemical reaction between the analyte (e.g., protein of interest to be detected in the biological sample) and the detection reagent. The detection reagent may be pre-loaded onto the sample receiving material. In one embodiment, the biological sample (e.g., the urine) when added to the sample receiving pad dissolves the detection reagent, and then the sample and detection reagent dye mix are transported across the device by flowing through the sample pad to contiguous material such as the trap.

Alternatively, the sample pad comprises a series of two or more sample pads (see, for example, FIG. 4). For example, the first pad may receive the sample and the second may contain the detection reagent, whereby the biological sample migrates from the first to the second element (pad) containing a detection reagent in a dried format suitable for an optimized chemical reaction between the analyte of interest and the detection reagent. If two or more sample receiving materials are utilized, either one may comprise the detection reagent. Preferably, the first sample receiving material comprises the detection reagent and the second sample receiving material does not.

In yet another embodiment, a first sample pad receives the biological sample and is designed to separate out or retain insoluble material that may be present in the sample. The filtered sample then flows through the first sample pad or to the second pad and the detection reagent is incorporated in either the first or second sample pad and allows for suitable mixing of the detection reagent and sample. The second pad may have the same or different composition as the first pad.

Further, in yet another embodiment, the first sample pad receives the sample and also contains the detection reagent, and the second pad provides for additional time for the mixing of detection reagent with the analyte of interest before entering the next contiguous material in the strip for example, the trap.

In an additional embodiment, the sample receiving material comprises a substrate for the detection reagent and retains the substrate upon drying. The detection reagent may be on or within the sample receiving material. Once the patient sample is added, the detection reagent is released. The substrate does not react with or absorb the patient sample which, when applied, moves through the matrix and onto contiguous material, for example, the trap.

It should be noted that the sample may be applied or placed into a cassette or housing, for example, through a sample well or other entity of the device for receiving the sample. The sample well or entity may be positioned over the sample receiving material of, for example, a test strip when it is assembled or encased inside a cassette or housing. (See FIG. 1.)

Materials useful as sample receiving material or sample pads are generally known in the art of lateral flow devices and chromatography [see Ref: EMD Millipore Rapid Lateral Flow Test Strips Considerations for Product Development, available from EMD Millipore, Billerica, Mass.] and are selected based on physical and chemical properties that impact sample receipt, controlled and even capillary flow, and sample filtering. Additionally, if the sample receiving material also contains the detection reagent, ideally, the material is a suitable matrix for holding the detection reagent and optimally releasing it upon addition of the test sample. The pad materials are porous, often made with cellulose (e.g., filter papers), glass fibers, woven meshes, synthetic, nonwoven material or porous plastic, for example, polyesters. Other materials that can be used as sample receiving material are, for example, polysulfone asymmetric membranes, cotton/glass fibers materials such as Ahlstrom® 8950, plastic polymer membranes, for example, polyethylene, (e.g. high density polyethylene), polytetrafluoroethylene, and porous glass fiber membranes (see, for example Porex, Fairburn, Ga.). See Examples for further description of materials (i.e., Examples 2 and 6).

It should be noted that the sample receiving material used in a device of the present invention, when the detection reagent is a dye with affinity to cellulose, may be cellulose provided enough detection reagent is present for binding to the modified protein or proteins of interest in the biological sample. More specifically, the cellulose cannot be permitted to "out compete" the detection reagent in connection with binding to the protein of interest, e.g., the misfolded protein or proteins in the biological sample. Alternatively, cellulose may be used for the sample receiving material if it is present in a matrix which is less reactive with the detection reagent than the modified proteins or protein of interest. (Cellulose, for purposes herein, is defined as an organic compound with the formula $(C_6H_{10}O_5)_n$ and, in particular, is a polysaccharide consisting of a linear chain of several hundred to many thousands of $\beta(1\text{->}4)$ linked D-glucose units.)

Trap

Next, the fluid (e.g. sample or sample mixed with detection reagent) flows from the sample receiving material or sample pad through a filter (hereinafter referred to as a "trap") designed to retain any unbound detection reagent. In particular, the trap serves to separate free detection reagent (e.g., dye) from protein-bound detection reagent in the lateral flow device. Specifically, the trap material permits the flow of sample through to the next contiguous material but retains, retards the flow of, or binds to the unbound detection reagent if the protein or proteins of interest are not present in the biological sample.

The trap abuts but preferably overlaps with the sample pad that contains the detection reagent (e.g., dye) or the series of sample pad elements (see, for example, FIG. 3). The trap functions to separate the detection reagent that is bound to the test sample protein or proteins of interest (e.g., misfolded protein or proteins) from detection reagent that is not bound to test sample protein or proteins, thus permitting the bound detection reagent to flow through while retaining the unbound detection reagent. Alternatively, the trap may be a series of one or more filters of the same or different materials.

Not to be bound by theory, the trap material may contain a substrate for the detection reagent such that unbound detection reagent binds the trap material and does not flow to the next material. Detection reagent that is already bound to proteins does not bind to the substrate in the trap and does flow to the next material in the strip. The substrate may be the trap material (e.g. cellulose) or it may be a chemical modification or addition to the trap material. Alternatively, a structural feature of the trap material composition may provide for the retention of unbound detection reagent.

Also, the trap may be comprised of multiple pieces of material overlapped or in succession to optimize for retaining unbound detection reagent (see FIG. 4). The multiple pieces may be the same or made from different materials. Filter matrices may be used for the trap, for example cellulose, thermoplastic polymers such as asymmetric polysulfone membrane (including but not limited to Vivid™ plasma separation membrane and asymmetric sub-micron (BTS) polysulfone membrane). See Examples for further description of trap materials (e.g. Examples 2, 4, 5, 8, 13, 14 and 16).

It was unexpected and quite surprising that there were, indeed, many nitrocellulose materials that actually worked well and permitted flow of urine and dye-bound proteins through the device. For example, Whatman® AE99 nitrocellulose membrane worked very well. (See Table 1.) There were also cellulose materials that worked reasonably well (for example, Ahlstrom® 601, 319, 247, Whatman® CF1, CF3, CF4; EMI11513, 5475, 5493), but there were also some cellulose materials that did not perform well (for example, Ahlstrom® 270). Surprisingly, among the materials that performed well for allowing protein-bound CR dye to flow while retaining unbound dye were Vivid™ Plasma separation materials (Pall Corporation) and asymmetric sub-micron (BTS) polysulfone membrane (Pall Corporation). (See Tables 1 and 2.)

When the detection reagent is a dye such as Congo red, the trap material may be, for example, filter papers, cellulose based and/or materials such as EMI 11513, EMI 5475, EMI 5493, 1281, 642, Standard 17, C048, LF1, LF1, VF2, CF1, CF3, Ahlstrom 319. The trap may be, for example, about 5-10 mm in length, or it may be a series of pieces each 5-10 mm in length.

In one embodiment, the trap retains free detection reagent (e.g., dye) but allows protein-bound dye to flow through. In a specific embodiment, the trap is comprised of cellulose and the detection reagent is Congo Red.

Detection Reagent

The detection reagent is a substance which is reactive with a protein or proteins of interest in the sample. For example, the detection reagent may be a substance which is reactive with or has a binding affinity for the misfolded protein or proteins (e.g., congophilic proteins), aggregated proteins and/or supramolecular aggregated proteins present in a biological sample from a mammal, e.g. the patient sample. The detection reagent may be preloaded onto a reagent pad (for example, applied onto the reagent pad, or the reagent pad dipped into the detection reagent or dye. The reagent pad may be the sample receiving material or sample receiving pad.

In one aspect, the detection reagent is a dye that stains the subset of proteins of interest in the biological sample, if present. In one embodiment, the detection reagent may react with misfolded proteins. For example, the dye may be an azo dye such as Congo Red (CR), or analog thereof, either buffered or unbuffered. Alternatively, other dyes could be used as detection reagents as long as these dyes have an affinity for (and can bind to or react with) the misfolded proteins, aggregated proteins and/or supramolecular protein or proteins of interest in the biological sample or patient sample. Examples of such dyes include but are not limited to Congo Red analogs such as those described in the following publications: Sellarajah S et al, *Synthesis of analogues of Congo red and evaluation of their anti prion activity*, J Med Chem. 2004 Oct. 21; 47(22):5515-34; and Hélène Rudyk et al, *Screening Congo Red and its analogues for their ability to prevent the formation of PrP-res in scrapie-infected cells*, Journal of General Virology (2000), 81, 1155-1164. The detection reagent for detecting misfolded protein or proteins may also be, for example, Thioflavin T.

Further, in one aspect of the invention, the detection reagent is present in a dried form in the device, but may be present in other forms as well. The form of detection reagent is suitable for optimally mixing with the sample when applied and allowing binding to the protein of interest. The form of the detection reagent is suitable for long term stability or shelf life of the device. In one embodiment, the dried detection reagent is a dye. Furthermore, the dye may be an Congo Red and may be present in the device in an amount of, for example, 0.1 ug to 800 ug, more preferably, 0.2 ug to 480 ug, even more preferably 1 ug to 400 ug, and even more preferred 2.5 to 120 ug.

Congo Red (CR) (e.g., buffered or non-buffered) may be pre-applied to the sample receiving material. For example, a CR solution can be applied to the material during kit manufacture and dried before assembly and packaging (see FIG. 2 and Example 6).

The detection reagent is detectable, i.e., visible to the naked eye, or otherwise detected, for example, by visual examination and/or mechanical or electronic reader(s).

The present invention provides for the detection reagent to be incorporated into the test device, for example, during manufacturing or assembly of the device. This is an improvement over previous devices for detecting misfolded proteins, where dye and biological sample needed to be mixed prior to adding to a test. In a preferred embodiment, the test strip contains a sample receiving material that contains the detection reagent. When the biological sample is added to the test device, into the sample receiving material, it mixes with the detection reagent in the sample receiving material and the biological sample-detection reagent mixture flows through the device.

Capillary Bed ("Display Strip")

A sample (e.g., urine) with or without protein-bound-detection reagent passes through the trap and onto a capillary bed (hereinafter referred to as a "display strip") where it accumulates. Thus, the display strip permits the flow of sample up the strip and displays the presence or absence of the detection reagent. In particular, the display strip permits the flow of sample up the strip and displays the presence or absence of the detection reagent-bound analyte. The detection reagent or bound reagent can then be visualized by human or mechanical means (to obtain a qualitative result) and/or then measured (i.e., semi-quantitatively or quantitatively). The display strip optimally provides for even flow of the sample throughout and relatively homogeneous display of the detection reagent when protein of interest is present. In certain embodiments, the intensity or concentration of the detection reagent on the display strip may correspond to the amount of protein of interest in the sample. In another embodiment, the distance the detection reagent flows up the display strip may be indicative of the amount of protein of interest in the biological sample. Furthermore, both the intensity of detection reagent and the distance up the display strip may be indicative the concentration of proteins in the sample. Furthermore, in the case of detection of misfolded protein aggregates or supramolecular aggregates, both the intensity of detection reagent and the distance up the display strip may be indicative the size of protein aggregates present in the sample. Suitable materials for the capillary bed include, for example, nitrocellulose or chromatography papers. Also, polysulfone asymmetric membranes provide suitable display strips. Other suitable materials include CytoSep® membranes such as CytoSep® 1660 and MN-260. The capillary bed of the lateral flow strip is aligned under a results viewing window of the lateral flow strip cassette or housing, described below. See Examples for further details of materials (e.g. Example 2, 3 and 9). If protein bound detection reagent is present, then the detection reagent is visualized within the window. (See FIG. 1.)

Wick

Optionally, the device contains a wick. The wick may be positioned after the third zone or the display strip in the strip or device of the invention. When in use, the biological sample (e.g., fluid) applied to the device continues to migrate from the display strip into a final porous absorbent material, the "wick", that acts as a sample accumulator and also may function to pull sample along the strip. Absorbent pads may be used, for example, as a wick at the end of the device strip to pull sample through the lateral flow strip, and may increase the amount of sample assayed and enhance assay sensitivity. These absorbent pads are often cellulose or cotton linters and optimally selected based on thickness, compressibility and uniformity of bed volume.

Backing Card

The device may have a backing card. The entire strip may be assembled on a backing card (for example, those available from Lohmann, Orange, Va.) which is often a card of a plastic backing and adhesive.

Housing/Cassette

In one embodiment of the present invention, the diagnostic device is housed, encased or encapsulated in a housing or cassette. The device may further comprise a housing or cassette, including but not limited to, a cartridge, plastic device or extruded plastic piece configured for the purpose, that encases the device. Several generic cassette housings are commercially available (for example, from Kanani Biologicals, Gujarat, India or EASE-Medtrend Biotech LTD, Shanghai, China) or may be custom-produced for the purpose at hand. (See, for example, U.S. Design patent application. Ser. No. 29/533,647.) The device may be configured in a housing or cassette having a sample well for receiving the sample, wherein the sample well is positioned over the sample receiving material of the strip when it is assembled/housed inside the cassette. Furthermore, the device may be configured such that, when assembled in the housing or cassette, the display strip or capillary bed of the strip is positioned beneath a result viewing window of the housing.

In one embodiment, the device of the invention also comprises an electronic reader that is able to quantify the result, e.g. the intensity of the detection reagent (e.g., dye) on the capillary bed (i.e., in the results window) and may further comprise a display screen (e.g., an LED screen) to display the results. This reader may be part of the housing, or an element that is assembled integrally with the housing, for example, in the results display window. Such readers are described, for example, in Venkatraman, *Biosensors and Bioelectronics Volume* 74, 15 Dec. 2015, Pages 150-155, PCT Application No. WO2013083686 A1, PCT Application No. WO2004010143 A2, and PCT Application No. WO2006010072 A2.

Cover Tape

The device with or without a housing may further comprise a cover such as a protective adhesive tape (for example, available from Lohmann, Orange, Va.) or other material capable of protecting the device from damage and providing for proper reading of test results. For example, the device may be configured to be used as a dipstick such as a urine dipstick. In this embodiment, the lateral flow strip may be covered with a protective adhesive tape. (See FIG. 5 and Example 11)

Run Control Reagent

In a preferred embodiment, a control reagent may be present on the capillary bed visible in the view window before the device is used. (See FIG. 1 and FIG. 2, Example 12.) When the biological sample (e.g., fluid) flows through the capillary bed, the control reagent dissolves, the control reagent line disseminates and/or the control is carried away, up the display strip so that no control reagent is visible in the results window, or it is blurred, or some other difference may be visualized or measured. The change in the control reagent in the view window indicates that the test sample (e.g., fluid) was added and has run through the device properly, e.g., serves as a run control. (See Example 12.) The control reagent is detectable visually e.g. by the naked eye or otherwise detected or measured, for example, by mechanical examination and/or an electronic reader. In one embodiment, the control reagent is tartrazine. Other dyes that may be used as the run control reagent include: FD&C Blue No. 1—Brilliant Blue FCF, E133 (blue shade), FD&C Blue No. 2—Indigotine, E132 (indigo shade), FD&C Green No. 3—Fast Green FCF, E143 (turquoise shade), FD&C Red No. 3—Erythrosine, E127 (pink shade), FD&C Red No. 40—Allura Red AC, E129 (red shade), FD&C Yellow No. 5—Tartrazine, E102 (yellow shade), FD&C Yellow No. 6—Sunset Yellow FCF, E110 (orange shade).

Detected Proteins of Interest

As noted above, the present invention is directed to a device and methods of utilizing this device for detection of proteins of interest, more specifically, misfolded proteins, aggregated proteins and/or supramolecular protein aggregates. It is known that the alpha helix is the prominent structural motif of the functional protein in its native conformation. In contrast, a conformational change in a protein can lead to a beta sheet structural motif (i.e., beta sheet structure) or a misfolded protein that then tends to cause protein aggregation and toxicity. The misfolded proteins may therefore be in the form of protein aggregates or supramolecular aggregates and may be associated with misfolded protein disorders such as preeclampsia, Alzheimer's disease, prion disease and Parkinson's disease.

In particular, these misfolded proteins, protein aggregates and/or supramolecular aggregates associated with preeclampsia which are detected by the device and methods of the present invention may include, but are not limited to, for example, alpha-1 antitrypsin (SerpinA1), ceruloplasmin, heavy-chain IgG, light-chain IgG, interferon-inducible protein 6-16 (IF16-6, G1P3), albumin as well as fragments of each protein, mixtures thereof, and fragments of such mixtures. These proteins have binding affinity for the detection reagent (to be described below) utilized in the device of the present invention. For example, these misfolded proteins are congophilic, having an affinity for the dye referred to as Congo Red.

The device of the present invention may also be used to detect protein-misfolding disorders other than preeclampsia. For example, the device may be utilized to detect misfolded proteins in such misfolded protein disorders or conditions as Alzheimer's disease, Cerebral beta-amyloid angiopathy, Retinal ganglion cell degeneration in glaucoma, Prion diseases, Parkinson's disease and other synucleinopathies, Tauopathies, Frontotemporal lobar degeneration (FTLD), FLTD-FUS, Amyotrophic lateral sclerosis (ALS), Huntington's disease and other triplet, repeat disorders, Dementia (familial British and Danish), Hereditary cerebral hemorrhage with amyloidosis, CADASIL, Alexander disease, various amyloidoses, Serinopathies, Type II diabetes, Inclusion body myositis/myopathy, cataracts, Retinitis pigmentosa with rhodopsin mutations, Medullary thyroid carcinoma, Pituitary prolactinoma, Hereditary lattice corneal dystrophy, Mallory bodies, Pulmonary alveolar proteinosis, Odontogenic tumor amyloid, Cystic fibrosis, Sickle cell disease and Critical illness myopathy.

Biological Sample

The protein or proteins of interest to be detected may be found in a biological sample from a mammal. The biological sample may be, for example, urine obtained from a clean or natural catch, cerebrospinal fluid, amniotic fluid or any bodily fluid sample potentially comprising the protein or proteins of interest (e.g., blood, saliva, amniotic fluid, cerebrospinal fluid, plasma or serum). The sample may also be an extract of excretions from a patient, for example, from nasal secretions, fecal material, or ear wax, or tissue specimens extracted with appropriate solutions and applied to the device. The proteins of interest may be found, for example, in a biological sample from a pregnant or postpartum mammal.

Patient

The patient may be a mammal. Furthermore, the mammal may be pregnant, for example, a pregnant woman, a pregnant primate or a genetically-engineered animal model designed to have the physical symptoms and signs of preeclampsia such as those utilized in laboratory studies (e.g., high blood pressure and protein in the urine). Preferably, for the diagnosis of preeclampsia, the patient may be any pregnant woman. The pregnant woman may be suspected of having preeclampsia or at risk of having preeclampsia. For example the suspicion may be based upon the following: 1) exhibiting the signs and symptoms of preeclampsia, for example, as set forth in the American College of Obstetrics and Gynecology Guidelines (ACOG) (Hypertension in Pregnancy, Report of the American College of Obstetricians and Gynecologists' Task Force on Hypertension in Pregnancy, Obstetrics and Gynecology 122 Vol. 122, No. 5, November 2013), specifically, for example TABLE E-1 (the "ACOG 2013 guidelines") and/or 2) having one or more risk factors for preeclampsia (e.g., a woman having a previous pregnancy involving preeclampsia, a woman carrying multiple fetuses, a woman with cardiovascular or renal abnormalities or a woman having an autoimmune disease such as lupus).

Kit

The present invention also includes a kit for detecting proteins of interest in a sample. In one embodiment, the kit comprises a device for detection of misfolded proteins associated with preeclampsia, present in a sample from a pregnant mammal. The kit comprises the device of the invention as described above in any alternative embodiments described above. The kits may also comprise a means for applying the patient sample to the sample receiving material, for example, a pipette (for example Fine tip transfer pipette available from Genesee Scientific, San Diego, Calif.) or dropper, a control as well as instructions for use of the device. Thus, not only may the device be utilized as a stand-alone entity, it may also be used in kit form which may be more advantageous in some clinical or non-clinical settings. The kit may be packaged in a foil or mylar pouch. Kit pouches may furthermore be packaged singly, or in multiples, e.g., 2, 5, 10, 15, 25, 50 or 100 kits per package.

Settings for Use of Device and Methods Utilizing Device

The device of the present invention may be used in, for example, clinical laboratories (either within a hospital setting or outside a hospital setting), immediate care settings, physician office laboratories, emergency departments (e.g., within a hospital) or as a near-patient testing or point-of-care device by medical personnel, non-medical professionals or even by the patient herself when the patient is a human. Further, the device may be used in combination with other diagnostic assays (e.g., immunoassays such as those that detect other proteins (i.e., biomarkers) associated with preeclampsia such as, for example, sFlt-1, PlGF, PP-A, PP13, pentraxin, inhibin-A and soluble endoglin), and/or other methods or observations commonly utilized in the diagnosis of preeclampsia (e.g., blood pressure readings, clinical tests used in the diagnosis of preeclampsia including platelet count, serum creatinine concertation, serum ALT (alaninine aminotransferase) and AST (aspartate aminotransferase), and other signs or symptoms such as weight gain, dizziness, headaches, blurred vision, etc.

For example, the present invention includes a method of diagnosis of preeclampsia or performing a differential diagnosis in a patient suffering from a hypertensive disorder of pregnancy or a patient who may be suspected of having preeclampsia comprising the steps of: a) determining a blood pressure of the pregnant patient, wherein a blood pressure greater than 140/90 mm/Hg in the pregnant patient may indicate preeclampsia in the pregnant patient and b) applying a biological sample from the patient to the device of the present invention, whereby detection of at least one protein of interest in the biological sample of the patient provides or supports a diagnosis of preeclampsia in the patient or acts as a differential diagnosis.

Further, the present invention also encompasses a method of treating a pregnant mammal suspected of having preeclampsia comprising the steps of: a) applying a biological sample from the mammal to the device of the present invention in order determine the presence of the at least one protein indicating the pregnant mammal has preeclampsia; and b) delivering the pregnant mammal in order to treat the preeclampsia. Further, the device may also be used post-delivery to determine if the patient is expressing the misfolded protein or proteins in the biological sample. If the misfolded protein or proteins are present, further patient management or therapeutic intervention may be needed (e.g., administration of magnesium sulfate or other antihypertensive agents) to treat the preeclampsia or the patient may be monitored using the device of the present invention to indicate when proteins are no longer detectable in the biological sample. Additionally, the device of the present invention may be utilized after therapeutic intervention to determine if treatment was successful or to measure a change (e.g., decrease, absence or increase) in the amount or presence of protein of interest present in the biological sample. Thus, the device of the present invention may be used pre- and post-treatment of the patient to determine whether further therapeutic intervention is necessary, to determine whether therapeutic intervention has been effective and/or whether to administer an alternative form of therapeutic intervention or an increased dosage of the therapeutic agent to resolve the preeclampsia or other protein-misfolding disorder.

Advantages of Device and Methods Utilizing the Device

The devices of the invention are advantageous over existing devices for at least the following reasons: 1) the device provides for a simplified testing procedure with fewer steps; 2) the device provides for the use of standardized test materials for optimal manufacturing; 3) the device provides for improved stability of the detection reagent in the test kit to provide a longer shelf life; 4) results are simpler and easier to read all while 5) retaining relatively low cost; and 6) providing fast results suitable for point-of-care use or use in clinical laboratory settings.

In particular, the provided device and methods are vastly superior to known paper kits for detecting possible preeclampsia (see, e.g., U.S. Patent Appln. Publication No. 20150293115) in that the provided device requires fewer steps for the user, results are easier to read and is more stable than the paper kits resulting in a long shelf life of at least 6 months, preferably 1 year, even more preferably 2 years, even more preferably 3 years, even more preferably 4 years, and even more preferably 5 years. The device of the invention also provides fast results (i.e., within 3 minutes, preferably within 2 minutes, and more preferably within 1 minute or less from application of the biological sample (e.g., urine) to the device) suitable for point-of-care users with minimal training.

The present invention may be illustrated by the use of the following non-limiting examples:

EXAMPLES

Example 1

Sample Devices

FIG. 1 shows photographs of device test strips of the invention in a cassette or housing. The left panel of FIG. 1 illustrates the device in a housing prior to contact with a biological sample. The right panel shows the device results of testing urine samples known to be negative, weak positive and positive for misfolded proteins associated with preeclampsia.

FIG. 2 shows an example of a test strip embodiment of the inventive device. The strip comprises a control dye, a display strip, a trap (e.g., three pieces of material), a second sample pad, a first sample pad and the dye dried onto the sample pad.

Figures 3A, 3B, 3C:
FIG. 3A shows a top view with a sample pad, a trap and a display strip.
FIG. 3B shows the same embodiment as in FIG. 3A viewed from the side. The sample pad, trap and display strip may be butted together.
FIG. 3C shows an embodiment with the sample pad, trap and display strip overlapping each other (side view).

FIG. 3A shows one embodiment of the diagnostic device of the present invention. FIG. 3A shows a top view. Figure B shows the same embodiment as in FIG. 3A but viewed from the side. The sample pad, trap and display strip may be butted together. FIG. 3C shows an embodiment with the sample, pad, trap and display strip overlapping each other (side view).

Figure 4A:
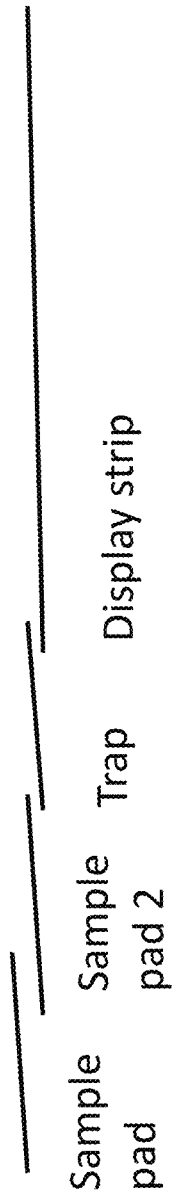
FIG. 4A shows an alternative embodiment of the invention having two sample pads, and a trap and display strip (capillary bed) in sequence each piece having an overlap with the adjacent piece.
Figure 4B:
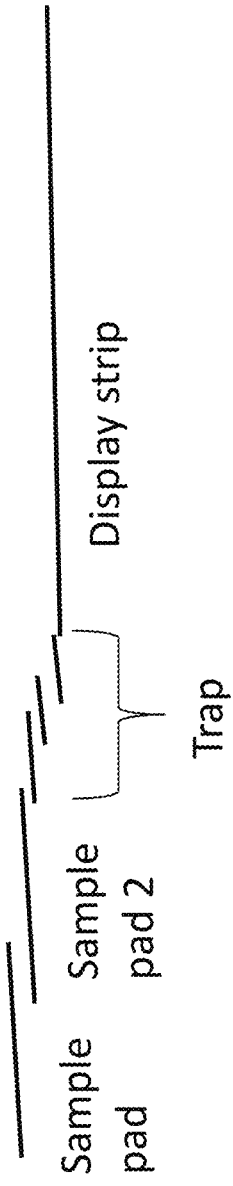
FIG. 4B shows another, alternative embodiment of the invention having two sample pads, a triple trap and a display strip overlapping in sequence, with each piece having an overlap with the adjacent piece.

FIG. 4 shows different material configurations within the test strip. FIG. 4A shows an alternative embodiment of the invention having two sample pads, a trap and a display strip (capillary bed) in sequence. Each piece has an overlap with the adjacent piece. FIG. 4B shows another, alternative embodiment of the invention having two sample pads, a triple trap and a display strip which overlap in sequence, each piece having an overlap with the adjacent piece.

FIG. 5 shows an example of a dipstick configuration of the test strip of the present invention. This embodiment is configured with a cover tape on top of the test strip. At the top of the test strip, the tape is opaque in color and may be used to hold the strip. In the middle, the tape is clear to provide a viewing window for the results. The tape may be placed so that the clear window is, for example, approximately 10 mm above the trap. The tape at the window may be surrounded by a color (e.g., white) which allows for easy viewing of the results. Below the trap, the tape is opaque in color to cover the trap. At the bottom of the strip, the tape may display an arrow indication as to which end of the strip to dip into the test sample and may display a line indicating the maximum level to dip the test strip into the sample. The bottom end of the test strip may be free of cover tape to facilitate wicking of test sample upon dipping.

Example 2

Materials Testing

Various paper-like materials were tested for ability to differentiate urine samples from pregnant women with and without preeclampsia. Congo Red (CR) dye (Sigma. St. Louis, Mo.) was added to urine samples and a drop was added to the material to assess characteristics suitable for sample receiving, trap and display strip. The resulting spot was visualized after about 3 minutes and evaluated for a visual difference between urine from preeclampsia patients and that from normal control pregnancies (Table 1). A result of "excellent" indicates the material was suitable in providing a visually observable difference between CR-urine from preeclampsia patients and CR-urine from control pregnant patients such that the material could be useful in the diagnostic test device. A result of "poor" indicates the material was not suitable in providing a visually observable difference between CR-preeclampsia positive and CR-control urines. From a scale from a result of "poor" being the least suitable material, "subtle" was slightly better but not ideal, "okay" better yet, "good" even better, "better" more improved and "excellent" being the most suitable materials. It was determined that the polysufone asymmetric materials provided the best results. Certain cotton materials such as CF3 and CF4 worked well whereas other cottons like Ahlstrom 270 did not work well. Nitrocellulose and glass fiber materials generally did now work well for this purpose.

TABLE 1

| Manufacturer | Material | Composition | Results |
| --- | --- | --- | --- |
| Pall Corp, Port Washington, New York | Vivid | polysulfone asymmetric | Excellent |
| Pall Corp | BTS | polysulfone asymmetric | Excellent |
| Whatman, GE Healthcare Bio-Sciences, Pittsburgh, PA | AE98 | Nitrocellulose | Okay |
| Whatman | AE99 | Nitrocellulose | Better |
| Whatman | FF120 | nitrocellulose on plastic | Good |
| Whatman | FF170HP | nitrocellulose on plastic | Poor |
| Whatman | FF85 | nitrocellulose on plastic | Subtle |
| Whatman | FF80HP | nitrocellulose on plastic | Subtle |
| Whatman | Prima 40 | Nitrocellulose | Okay |
| Whatman | Prima 125 | Nitrocellulose | Less so |
| Whatman | Immunopore RP | | Subtle |
| Whatman | Standard 14 | glass fiber | Poor |
| Whatman | Standard 17 | glass fiber | Poor |
| Whatman | CF3 | Cotton | Okay |
| Whatman | CF4 | Cotton | Okay |
| Whatman | VF2 | | Poor |
| Whatman | LF1 | | Subtle |
| Millipore, EMD Millipore, Billerica, MA | HF75 | Nitrocellulose | Modest |
| Millipore | HF90 | Nitrocellulose | Modest |
| Millipore | HF120 | Nitrocellulose | Poor |
| Millipore | HF135 | Nitrocellulose | Poor |
| Millipore | HF170 | Nitrocellulose | Poor |
| Millipore | HF180 | Nitrocellulose | Poor |
| Sartorius Stedim, Bohemia, New York | CN150 | Nitrocellulose | Subtle |
| Sartorius Stedim, | CN140 | Nitrocellulose | Subtle |
| Sartorius Stedim, | CN95 | Nitrocellulose | Subtle |
| Ahlstrom, Helsinki Finland | 270 | Cotton | Poor |
| Ahlstrom | 222 | | Poor |
| Ahlstrom | 320 | | Poor |
| Ahlstrom | 111 | Glass | Poor |
| Ahlstrom | 142 | Glass | Poor |
| Ahlstrom | 21 | | Poor |
| Ahlstrom | 141 | Glass | Poor |
| Ahlstrom | 6613 | glass or polyester | Poor |
| Ahlstrom | 6615 | | Poor |
| Ahlstrom | 181 | | Poor |
| Ahlstrom | 169 | | Poor |
| Ahlstrom | 161 | | Poor |
| Ahlstrom | 151 | | Poor |
| Ahlstrom | 131 | | Poor |
| Ahlstrom | 601 | Cotton | Good |
| Ahlstrom | 237 | | Okay |
| Ahlstrom | 238 | Cotton | Subtle |
| Ahlstrom | 8950 | cotton or glass | Poor |
| Ahlstrom | 8951 | glass fiber or polyester | Poor |
| Ahlstrom | 8964 | glass fiber | Poor |
| Ahlstrom | CytoSep 1662 | Proprietary | Good |
| Ahlstrom | CytoSep 1663 | Proprietary | Good |
| Ahlstrom | CytoSep 1660 | Proprietary | Good |
| Ahlstrom | ReliaFlow 319 | | Subtle |
| Ahlstrom | ReliaFlow 800 | | Poor |
| Ahlstrom | ReliaFlow 1281 | | Subtle |
| Macherey Nagel Bethlehem, PA | MN-260 | | Good |
| Macherey Nagel | MN-321 | | Subtle |
| Macherey Nagel | MN-615 | | Good |
| Macherey Nagel | MN-616g | | Okay |
| Macherey Nagel | MN-640 | | Okay |

TABLE 1-continued

| Manufacturer | Material | Composition | Results |
| --- | --- | --- | --- |
| Macherey Nagel | MN-6176 | | Okay |
| Lypore Rochester, NH | 9334 | | Poor |
| Lypore | 9390 | | Poor |
| Lypore | 9389 | | Poor |

Example 3

Test Strip

Test strips were assembled using a Ahlstrom® 8950 (a cotton/glass fiber composition)("8950") sample pad and a BTS or Vivid™ running strip or capillary bed, as BTS and Vivid had demonstrated excellent results in providing a visually observable difference between CR-urine from preeclampsia patients and CR-urine from control pregnant patients. Congo Red was added to urine samples, the sample was vortexed, and then samples were applied to the 8950 end of the test strip. Results were observed on the BTS or Vivid™ membrane run strip. Urine from women with preeclampsia applied to Vivid™ membrane containing strips resulted in very clear signal (pink/red Congo Red staining) with negative urines showing no signal. Signal was volume dependent with decreasing volumes resulting in decreasing signal. The BTS strips showed no difference between positive and negative urines with both resulting in positive staining at the higher sample volume. Signal decreased equally for the positive and negative urines with decreasing sample volumes applied.

TABLE 2

| Run Material | Positive Urine | Staining Results | Negative Urine | Results |
| --- | --- | --- | --- | --- |
| Vivid | 90 ul | Positive | 90 ul | Negative |
| Vivid | 50 ul | Weak positive | 50 ul | Negative |
| Vivid | 30 ul | Negative | 30 ul | Negative |
| BTS | 90 ul | Positive | 90 ul | Positive |
| BTS | 50 ul | Weak positive | 50 ul | Weak positive |
| BTS | 30 ul | Negative | 30 ul | Negative |

These results indicate that the Vivid™ material was suitable in the diagnostic test device of the present invention whereas the BTS did not perform well.

Example 4

Trap Materials Evaluation

Vivid™ and BTS membranes were evaluated as materials for the trap, that is positioned between the sample pad and the run strip (i.e., capillary bed or display strip) to determine if they aided in the retention of CR dye when negative urines (i.e., urine not containing the proteins of interest from a woman without preeclampsia) were applied, allowing CR with preeclampsia-positive urine to flow through to the display strip. Test strips were assembled to include 8950 as a sample pad with either Vivid™ membrane or BTS membrane followed by a CytoSep® 1660 run strip. Urine with added CR was applied to the 8950 and results were observed on the CytoSep® 1660 run strip.

CR staining was seen on all strips when positive urine (i.e., urine containing the proteins of interest from a woman with preeclampsia)—Congo Red dye was applied. While strips made with a Vivid™ membrane trap were negative when negative urine-Congo Red was applied, strips made with a BST membrane trap showed some dye staining. The Vivid™ material was an effective trap to retain CR dye when negative urine was tested, while letting through the CR dye when positive urine was tested. BTS was a less effective trap.

Example 5

Evaluation of Materials for Use for Pre-Loaded Detection Reagent in Test Strips

Congo Red dye was applied to sample pad materials and allowed to dry. Positive urine was applied and the results on the dye release from the sample pad were observed.

TABLE 3

| Material | Results |
| --- | --- |
| POREX ® 4894 (Porex, Fairburn, GA) | Good dye release and flow |
| Porex ® X-4897 | Good dye release and flow |
| Porex ® D3883B | Modest dye release, spot still retained |
| Porex ® PVA | Poor dye release, no flow |
| Fusion 5-1 (GE Healthcare Life Sciences, Pittsburgh PA) | Modest dye release spot still retained |
| Fusion 5-2 (GE Healthcare Life Sciences,) | Modest dye release spot still retained |
| GF DVA 1 (GE Healthcare Life Sciences,) | Poor dye release |
| GF DVA 2 (GE Healthcare Life Sciences,) | Poor dye release |
| Whatman ® 33 (GE Healthcare Life Sciences,) | Modest dye release, spot still retained |

The detection reagent (i.e., dye in this instance) ideally is released from the sample pad material upon application of the biological sample, i.e., urine. Several materials including POREX® 4894 and Porex® X-4897 provided for good dye release and therefore are highly suitable in the diagnostic test device. Additionally, several materials also provided dye release and are suitable, such as Fusion materials (glass microfibers) and Whatman® 33.

Example 6

Evaluation of Sample Pads with Dye Incorporated into Test Strips

Sample pad materials including Porex®, X4897 and POREX® 4894 infused with Congo Red dye were incorporated into test strips with a Vivid™ x trap and an MN-260 run or display strip. Urine was added to the sample pad of each strip and results observed on the MN-260 display strip.

Results: The sample pad materials released dye when urine was added. Adding preeclampsia-positive urines resulted in positive staining of the MN260 material. In most cases, adding preeclampsia-negative urines resulted in no staining of the MN260; however, in some cases there was some staining at the beginning of the MN260 strip. These results indicate that the configuration of Porex®, Vivid™, MN260 materials could provide means for differentiating preeclampsia positive from preeclampsia negative urines, providing for a useful diagnostic test device.

Example 7

Test Strip Evaluation in Lateral Flow Assay Cassette

Strips were assembled of dye infused POR-4899 sample pad, placed on top of Fusion 5, followed by Vivid X membrane serving as a trap and then MN260 display strip. Strips were placed in generic cassette with the sample pad directly underneath sample port of the cassette and the MN260 visible in the cassette results window. [75 ul] Seventy-five microliters of urine were added in the sample port and results were observed in the results window. When positive urines were added, Red staining was visible in the results window whereas, when negative urines were added, no staining was observed. This configuration provided for an effective diagnostic device differentiating preeclampsia positive from preeclampsia negative urines.

Example 8

Refining the Trap

At times, negative urine tested on the strip resulted in some streaking of dye up the results strip, particularly over time. Additional trap configurations were evaluated to see if better separation of positive vs. negative samples could be achieved and if this streaking with negative urines could be eliminated. Strips were assembled with dye infused POR-4899 sample pad placed on top of Fusion 5, a trap of two offset but overlapping layers of Vivid™ X and MN260 results strip. When tested by applying negative urines, the double layer trap prevented dye leakage and streaking thereby providing for an improved diagnostic test device for differentiating preeclampsia positive from preeclampsia negative urines.

Example 9

Device Strip Configurations

POR-4899 was striped with Congo Red dye solution dispensed at 6 μl/cm using a Kinematic dispensing machine. POR-4588 was striped at 4 μl/cm. Pads were dried at 37° C. for 1 hour and stored in a desiccant cabinet. Test strips were assembled using the striped POR material, one layer Vivid™ X trap and MN260. The POR-4899 strip performed well when testing urines; however, the strip containing POR-4588 resulted in dye leakage onto the display strip when testing negative urines. POR-4588 was further evaluated when striped at 4 μl/cm and resulted in clean negative urine run. Then, POR-4588 was evaluated when striped at 6 or 8 μl/cm assembled with a double Vivid™ trap. This strip assembly with 6 μl/cm dye strip gave the best results when testing positive urines and the least amount of dye leakage or streaking when testing negative urines. Further, evaluation of strip with a 3 layer Vivid™ trap and POR-4588 striped at 8 μl/cm gave good results and a stronger positive signal.

TABLE 4

| Dye pad | Congo red dispensing rate | Trap | Pos/neg differentiation |
| --- | --- | --- | --- |
| POR-4899 | 6 ul/cm | Single Vivid ™ trap | ✓ |
| POR-4588 | 4 ul/cm | Single Vivid ™ trap | False positive |

TABLE 4-continued

| Dye pad | Congo red dispensing rate | Trap | Pos/neg differentiation |
| --- | --- | --- | --- |
| POR-4588 | 6 ul/cm | Double Vivid ™ trap | ✓ |
| POR-4588 | 8 ul/cm | Double Vivid ™ trap | ✓ |

The device configured with POR-4599 with Congo Red applied at 8 ul/cm and a double vivid trap resulted in a clean, negative result when preeclampsia negative urine was tested and a strong positive result when preeclampsia positive urine was tested and therefore is a preferred diagnostic test device configuration.

Example 10

Evaluation of a Dipstick Format Test Design

Test strips were assembled using POR-4588 striped at 6, 8 or 10 μl/cm with a 3 layer Vivid™ trap and MN260. Strips were dipped into 60 μl of urine. Urine successfully wicked up the strip and the version with 8 μl/cm stripping provided the best positive test results with clean negative test results. Therefore, a suitable dipstick format of the diagnostic test device can be configured in this way and is useful for differentiating preeclampsia positive urine from preeclampsia negative urine for diagnostic purposes.

Example 11

Further Evaluation of Diagnostic Test Device Configuration

Test strips made of two Porex® sample pads, one striped with dye; 3 Vivid™ layer trap, and MN260 were tested in a cassette/housing and as dipsticks for testing urine. The cassette housing improved results, perhaps because of controlled flow of sample onto central spot on sample pad, good uptake of dye, flow up center of strip, and more homogeneous staining of run strip result. Five negative urines all tested negative; 5 positive urines resulted in 2 weak positive, 3 positive results. As a dipstick, the test strip was placed into 100 μl urine in a test tube. At 3 minutes, all results for both positive and negative urines were negative. However, given more time, by 5 minutes the positive urines results were 2 weak positives, 3 positives, while negative urines remained negative. Therefore, these test configurations are suitable preeclampsia diagnostic test devices.

Example 12

Evaluation of Run Control

The purpose of this experiment was to investigate a control that indicates when the sample has run up the strip successfully, a "run control". When a negative biological sample is tested and no staining is observed on the display or results strip it is difficult to tell if it is a negative result, or the test failed to run correctly (i.e., no sample was actually added, insufficient sample was added or insufficient wicking of the sample up the strip occurred). A stripe of a water soluble coloring was sprayed across the run strip material, positioned so that it would be visible in the top of the cassette results window when assembled in the housing. Urine samples were applied to the sample pad through the sample port and flow observed through the results window. When sample reached the control dye stripe, the stripe dissolved and ran with the sample. The disappearance of the run control stripe provided an easily visible indication that sample had run through the strip successfully. The control did not interfere with reading results of the urine test. An example of control strip dye is tartrazine. Other dyes that may be used as the run control include: FD&C Blue No. 1—Brilliant Blue FCF, E133 (blue shade), FD&C Blue No. 2—Indigotine, E132 (indigo shade), FD&C Green No. 3—Fast Green FCF, E143 (turquoise shade), FD&C Red No. 3—Erythrosine, E127 (pink shade), FD&C Red No. 40—Allura Red AC, E129 (red shade), FD&C Yellow No. 5—Tartrazine, E102 (yellow shade), FD&C Yellow No. 6—Sunset Yellow FCF, E110 (orange shade).

Example 13

Investigation of Alternative Materials for Trap

Test strips were assembled with 2 Porex® sample pads, the first striped with Congo Red (CR) dye, a variety of alternative trap materials as listed in Table 5 and MN260 run strip. Negative urine sample were tested on the assembled test strips and the ability of each trap to: 1) retain the CR dye when proteins of interest in the sample are not present and 2) not retain protein bound CR were evaluated.

TABLE 5

| Trap Material | Results testing Negative sample | Results testing Positive sample |
| --- | --- | --- |
| EMI 11513 (EMI Specialty Papers, Redding, CT) | Negative, slight dye run off | Positive |
| EMI 5475 (EMI Specialty Papers) | Negative, very little dye run off | Positive |
| EMI 5493 (EMI Specialty Papers) | Negative, slight dye run off | Positive |
| ReliaFlow 1281 | Negative, slight dye run off | Positive (streaky) |
| Ahlstrom 642 | Negative, very little dye run off | Positive |
| Whatman® Standard 17 | Negative, modest dye run off | Positive (streaky) |
| Millipore C048 | Negative, very little dye run off | Weak positive |
| Whatman® LF1 | Negative, slight dye run off | Weak positive |
| Whatman® VF2 | Negative, very little dye run off | Weak positive |
| Whatman® CF1 | Negative, slight dye run off | Positive |
| Whatman® CF3 | Negative, very little dye run off | Positive |

Results: Most of these trap materials showed promise in differentiating congophilic protein-positive biological samples (congophilic protein positive urine) from congophilic protein-negative biological samples (congophilic protein-negative urine).

To further improve the retention of detection reagent (CR) when negative samples are tested, test strips were then made using select trap material described in Table 6 in three layers.

TABLE 6

| Trap Material | Results testing Negative sample | Results testing Positive sample |
| --- | --- | --- |
| EMI 11513 | Negative | Weak Positive |
| 642 | Negative | Positive |

TABLE 6-continued

| Trap Material | Results testing Negative sample | Results testing Positive sample |
| --- | --- | --- |
| C048 | Negative | Weak positive |
| CF1 | Negative, slight run off | Positive |

Results: A triple layer trap was effective in retaining unbound CR detection reagent from entering the display strip. However, triple trap configuration made with EMI 11513 and C048 also reduced signal results intensity when testing positive samples. Triple traps made with 642 provided the best results for both positive and negative samples, amongst those traps tested.

Example 14

Further Investigation of Trap Materials

To further investigate suitable materials for use as a trap in the diagnostic test device of the present invention, strips with 2 Porex® sample pads, the first striped with CR dye (8 ul/cm), a trap as described in Table 7 and MN260 run strip were assembled. Strips of each configuration were tested with a congophilic negative urine sample, two weak positive congophilic protein samples and two strong positive congophilic protein samples.

TABLE 7

Investigation of trap materials as single layer

| Material | Neg | Weak positive | Strong Positive | Weak positive | Strong Positive |
| --- | --- | --- | --- | --- | --- |
| EMI 11513 | − | +− | | +− | ++ |
| 237 | − | + | ++ | + | ++ |
| 319 | − | + | ++ | + | ++ |
| CF1 | − | +− | ++ | +− | + |
| Vivid™ | − | ++ | ++ | +− | ++ |
| 5475 | − | + | ++ | +− | ++ |
| 5493 | − | +− | ++ | +− | ++ |
| C048 | − | +−− | + | +−− | + |
| CF3 | − | +−− | + | +−− | + |
| 238 | − | + | + | +− | + |
| 601 | − | + | + | + | + |
| 1281 | − | +− | + | +− | ++ |
| 642 | − | +− | + | +−− | + |
| MN640m | − | +− | + | +−− | + |
| MN615 | − | +− | ++ | +− | + |

Surprisingly, 5493 results were less intense than 5475, with 5493 about 4 times more absorbent and 2 times faster capillary rise characteristics than 5475. These results suggest that less absorption and a slower capillary rise is preferable for robust signal. Similarly, CF3 is weaker than CF1, having two times the absorption. Material 238 has a weaker signal than 237 and has twice the wick rate, and 319 showed the strongest color results of this paper line and had the slowest wick rate. MN640 which is a faster running material has weaker signal than MN615.

Results show that the materials that have less absorbency, slower capillary rise or wick rate may be preferred materials for more robust signal.

Example 15

Evaluation of Diagnostic Test Devices

A complete test strip was assembled, comprising a dye infused Porex® sample pad placed on top of Fusion 5 (a proprietary single layer matrix membrane made by GE), a Vivid™ membrane strip trap and MN260 capillary bed membrane. The strip was housed in a generic LFA cassette case. Urine samples were added to the circular sample well and results were observed in the rectangular window at 3 minutes.

Results: No dye was observed in the window for negative urine, a light pink was observed for weak positive urine and a strong pink was observed for the strong positive urine sample. These results indicate this is a suitable configuration for a diagnostic test device for detection of congophilic proteins in a sample for the diagnosis of preeclampsia.

Example 16

Further Evaluation of Optimal Trap Materials

A complete test strip was assembled, comprising a dye infused Porex® sample pad a second Porex® pad (without dye), a trap of single or double layers of 11513, 5475, 319, 247, or CF1, a MN260 membrane capillary bed with a wick of Whatman 470. The MN260 contained a run control stripe of tartrazine dye. The test strip was housed in a LFA-like cassette optimized for addition of test sample onto dye infused Porex® pad, and a view window centered over the MN260 membrane such that the tartrazine dye is observable prior to running the test and not observed after the test is run. Urine samples were added to the circular sample well and results were observed in the rectangular window at 3 minutes.

Results

No dye was observed in the window for negative urine, a light pink was observed for weak positive urine and a strong pink/red was observed for the strong positive urine sample at 3 minutes. Furthermore, the yellow tartrazine dye stripe was evident prior to adding sample, could be observed to travel along with the wicking of the sample, and was barely visible or completely gone at 3 minutes. These results indicate this is a suitable configuration for a diagnostic test device for detection of congophilic proteins in a sample for the diagnosis of preeclampsia.

Example 17

Results of Present Device Versus CRD Test Results

The test device of the present invention was evaluated by testing 105 clinical urine specimens from a study of the Congo Red dot (CRD) test in women suspected of preeclampsia (Rood et al., 2016 AJOG, 214(1)s24-s25). Samples were chosen to provide 27 strong positives, 28 negatives and 50 weak positive samples. The negative/positive status of the samples was determined by % CRR (Irina A. Buhimschi et al., *Sci. Transl. Med.* 6, 245ra92 (2014)). Samples were added to the test device and results were visually scored at 3 minutes as either negative (– or 0), weak positive (+ or 1) or strong positive (++ or 2).

Results showed that the test device results were concordant with the CRD result in 103/105 of the samples (98%). The test result of the device of the present invention, when compared to an adjudicated diagnosis of preeclampsia (based on ACOG guidance: Hypertension in Pregnancy Report of the American College of Obstetricians and Gynecologists' Task Force on Hypertension in Pregnancy, 2013 Obstetrics & Gynecology 122(5): 1122-1131), showed a sensitivity of 91%; specificity of 64%, accuracy of 82% with a positive predictive value of 83% and a negative predictive value of 79%.

Upon adding the test sample to the sample well of the test, the front of the liquid traveling up the strip was visible by 30 seconds. The front hit the yellow dye control stripe at about 1 minute and traveled to the end of the window by about 1.5 min. Strong positive results were clearly visible with the front of liquid traveling into the results window by 30 seconds and beyond. The full results window was colored by 1.5 min. Weak positive results take longer to resolve than the strong positives as the liquid front commonly appeared negative with color developing in the results window at about 1-3 minutes after addition of the sample. FIG. 1 shows examples of results.

Example 18

Evaluation of Device Using Urine Sample Controls

The device test strip was assembled, comprising a Porex® 4588 sample pad dye infused 120 ug/device, a second Porex® pad (without dye), a trap of double layers of Ahlstrom 319, a MN260 membrane capillary bed with a wick of Whatman 470. The MN260 contained a run control stripe of tartrazine dye. The test strip was housed in a LFA-like cassette optimized for addition of test sample onto dye infused Porex® pad, and a view window centered over the MN260 membrane such that the tartrazine dye is observable prior to running the test and not observed after the test is run.

Urine specimens from five (5) patients with confirmed preeclampsia were pooled to create a positive assay control. The presence of congophilic proteins was confirmed by the Congo Red dot blot test (Buhimschi 2014). Phosphate buffered saline (10 mM phosphate, pH 7.4, 150 mM NaCl) was used as a negative control and for making the dilution series of the positive assay control. The following dilution were prepared (in ratio of sample to total volume of buffer): undiluted, 1:4, 1:8, 1:15, 1:40. Each urine sample of the dilution series was tested in duplicate on the device.

Results: Each replicate for each urine sample for a particular dilution exhibit the same density of staining on the devices. The results of the testing are presented in the following table.

TABLE 8

Testing results from a dilution series of a pooled urine sample

| Dilution | Test Results |
| --- | --- |
| Undiluted | +++ |
| 1:4 | ++ |
| 1:8 | + |
| 1:10 | ± |
| 1:15 | ± |
| 1:40 | – |

These data demonstrate that the diagnostic device can detect congophilic proteins, and that the effect is titratable. These data also indicate that device exhibits a progressive visual scale of red color corresponding to increasing concentration of congophilic proteins.

What is claimed is:

1. A diagnostic device for detection of at least one protein in a biological sample of a mammal, comprising:
   a) a sample receiving material, wherein said sample receiving material is capable of receiving a biological sample;
   b) a detection reagent, wherein said detection reagent is present on or within said sample receiving material and binds to at least one protein present in said biological sample, wherein said detection reagent is selected from the group consisting of an azo dye, Thioflavin T and an analog of an azo dye;

c) a trap, wherein said trap is in contact with the sample receiving material and (i) separates detection reagent bound to said at least one protein in said biological sample from unbound detection reagent; (ii) permits flow of detection reagent bound to said at least one protein in said biological sample through said trap; and (iii) retains, retards the flow of, or binds said unbound detection reagent, wherein said trap is a material selected from the group consisting of nitrocellulose, cellulose, a glass fiber, a cotton fiber, a woven mesh, a nonwoven material, asymmetric polysulfone membrane, polyvinylidene fluoride and polyethersulfone;

d) a capillary bed, wherein said capillary bed is in contact with said trap, and wherein said capillary bed is configured to contain said biological sample after said biological sample flows through said trap, wherein said sample receiving material, said trap, and said capillary bed are configured to be in contact in sequence, and wherein said capillary bed displays detection reagent if said at least one protein is present in said biological sample.

2. The diagnostic device of claim 1, wherein said sample receiving material comprises said detection reagent.

3. The diagnostic device of claim 1, wherein said detection reagent is in dried form.

4. The diagnostic device of claim 1, wherein said sample receiving material releases said detection reagent into said biological sample subsequent to application of said biological sample to said sample receiving material.

5. The diagnostic device of claim 4, wherein said sample receiving material is a matrix for mixing of said detection reagent with said biological sample.

6. The diagnostic device of claim 5, wherein, subsequent to mixing of detection reagent and biological sample, said sample receiving pad releases mixed detection reagent and biological sample to said trap adjacent to said sample receiving pad.

7. A housing or cassette encasing said diagnostic device of claim 1.

8. The diagnostic device of claim 1, wherein said detection reagent binds to at least one protein selected from the group consisting of a misfolded protein, a protein aggregate, a supramolecular protein aggregate, a fragment of a misfolded protein, a fragment of a protein aggregate, a fragment of a supramolecular protein aggregate, and mixtures thereof.

9. The diagnostic device of claim 8, wherein said misfolded protein is selected from the group consisting of alpha-1 antitrypsin (SerpinA1), ceruloplasmin, heavy-chain IgG, light-chain IgG, interferon-inducible protein 6-16 (IF16-6,G1P3), albumin, and fragments thereof.

10. The diagnostic device of claim 1, wherein said at least one protein is congophilic.

11. The diagnostic device of claim 1, wherein said azo dye is Congo Red.

12. The diagnostic device of claim 11, wherein said Congo Red is pre-loaded onto said sample receiving material.

13. The diagnostic device of claim 1, wherein said sample receiving material comprises a material selected from the group consisting of nitrocellulose, cellulose, a glass fiber, a cotton, a woven mesh, a nonwoven material, a porous plastic, polymer and a polyester.

14. The diagnostic device of claim 13, wherein said polyester is polyethylene.

15. A kit comprising said device of claim 1.

16. The kit of claim 15 further comprising a calibrator or control reagent.

* * * * *